(12) United States Patent
Simske et al.

(10) Patent No.: US 11,992,411 B2
(45) Date of Patent: May 28, 2024

(54) ANCHORING DEVICE

(71) Applicant: Colorado State University Research Foundation, Fort Collins, CO (US)

(72) Inventors: Steve Simske, Fort Collins, CO (US); Adam Morrone, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 17/118,756

(22) Filed: Dec. 11, 2020

(65) Prior Publication Data

US 2021/0177609 A1 Jun. 17, 2021

Related U.S. Application Data

(60) Provisional application No. 62/947,970, filed on Dec. 13, 2019.

(51) Int. Cl.

| A61F 2/44 | (2006.01) |
|---|---|
| A61B 17/04 | (2006.01) |
| A61B 17/68 | (2006.01) |
| A61B 17/80 | (2006.01) |
| A61B 17/86 | (2006.01) |
| A61F 2/08 | (2006.01) |
| A61F 2/30 | (2006.01) |
| A61F 2/36 | (2006.01) |

(52) U.S. Cl.
CPC ........ *A61F 2/3609* (2013.01); *A61F 2/30771* (2013.01); *A61F 2002/30354* (2013.01); *A61F 2002/30878* (2013.01); *A61F 2310/00023* (2013.01)

(58) Field of Classification Search
None
See application file for complete search history.

(56) References Cited

U.S. PATENT DOCUMENTS

| 3,108,595 | A | * | 10/1963 | Overment | A61M 25/04 604/105 |
|---|---|---|---|---|---|
| 5,059,193 | A | * | 10/1991 | Kuslich | A61F 2/4455 606/279 |
| 5,203,773 | A | * | 4/1993 | Green | A61B 17/34 604/105 |
| 5,454,365 | A | * | 10/1995 | Bonutti | A61B 17/0218 606/198 |

(Continued)

*Primary Examiner* — Ann Schillinger
(74) *Attorney, Agent, or Firm* — Robinson IP Law, PLLC

(57) ABSTRACT

Various implementations include an anchoring device including a tubular body and at least one anchor. The at least one anchor extends along an opening between a first axial end and a second axial end of the opening. The at least one anchor includes a shape memory material. The at least one anchor is movable from a retracted position to an extended position by either increasing the temperature of the anchor above an austenite finishing temperature or decreasing the temperature of the anchor below a martensite finishing temperature. The anchor has a smaller radius of curvature in a plane that includes the longitudinal axis in the extended position than in the retracted position. When used as a coupler for medical implants, the device can be easily removed and reimplanted during re-surgery without damaging the bone of a patient by increasing or decreasing the temperature of the shape memory material anchors.

17 Claims, 5 Drawing Sheets

(56) References Cited

U.S. PATENT DOCUMENTS

| | | | | |
|---|---|---|---|---|
| 6,350,271 B1* | 2/2002 | Kurz | A61B 17/221 | 606/127 |
| 6,676,665 B2* | 1/2004 | Foley | A61B 17/025 | 606/105 |
| 6,780,175 B1* | 8/2004 | Sachdeva | A61B 17/221 | 606/198 |
| 6,783,530 B1* | 8/2004 | Levy | A61B 17/7275 | 606/62 |
| 7,621,950 B1* | 11/2009 | Globerman | A61B 17/1637 | 623/17.11 |
| 8,080,044 B2* | 12/2011 | Biedermann | A61B 17/7037 | 606/313 |
| 8,292,932 B2* | 10/2012 | Matthis | A61B 17/8625 | 606/313 |
| 8,529,628 B2* | 9/2013 | Marino | A61B 17/8858 | 623/17.11 |
| 8,657,860 B2* | 2/2014 | Biedermann | A61B 17/68 | 606/313 |
| 8,888,810 B2* | 11/2014 | Hadba | B21G 7/02 | 606/213 |
| 9,044,313 B2* | 6/2015 | Heaven | A61B 17/0401 | |
| 9,326,804 B2* | 5/2016 | Biedermann | A61B 17/7001 | |
| 9,452,003 B2* | 9/2016 | Voor | A61B 17/74 | |
| 9,462,721 B2* | 10/2016 | Jau | G11B 33/128 | |
| 9,724,141 B2* | 8/2017 | Thornes | A61B 17/746 | |
| 9,980,715 B2* | 5/2018 | Marino | A61F 2/0811 | |
| 11,045,237 B2* | 6/2021 | Biedermann | A61B 17/866 | |
| 11,109,897 B2* | 9/2021 | Suddaby | A61B 17/1617 | |
| 11,918,261 B2* | 3/2024 | Singh | A61B 17/8057 | |
| 2002/0165544 A1* | 11/2002 | Perren | A61B 17/7266 | 606/63 |
| 2004/0133204 A1* | 7/2004 | Davies | A61B 17/7266 | 606/62 |
| 2004/0167625 A1* | 8/2004 | Beyar | A61F 2/4657 | 623/17.11 |
| 2004/0230193 A1* | 11/2004 | Cheung | A61B 17/7266 | 606/63 |
| 2007/0282443 A1* | 12/2007 | Globerman | A61F 2/4657 | 623/17.11 |
| 2007/0293866 A1* | 12/2007 | Stoeckel | A61B 17/7266 | 606/326 |
| 2008/0262497 A1* | 10/2008 | Nijenbanning | A61B 17/744 | 606/62 |
| 2010/0298873 A1* | 11/2010 | Odermatt | A61B 17/06166 | 606/228 |
| 2011/0004308 A1* | 1/2011 | Marino | A61B 17/8858 | 219/121.72 |
| 2012/0289776 A1* | 11/2012 | Keast | A61B 10/0233 | 600/106 |
| 2013/0046346 A1* | 2/2013 | Thorwarth | B32B 27/28 | 606/281 |
| 2014/0067073 A1* | 3/2014 | Hauck | A61F 2/4465 | 606/279 |
| 2016/0345954 A1* | 12/2016 | Marino | A61F 2/0811 | |
| 2017/0258498 A1* | 9/2017 | Redmond | A61B 17/7055 | |

* cited by examiner

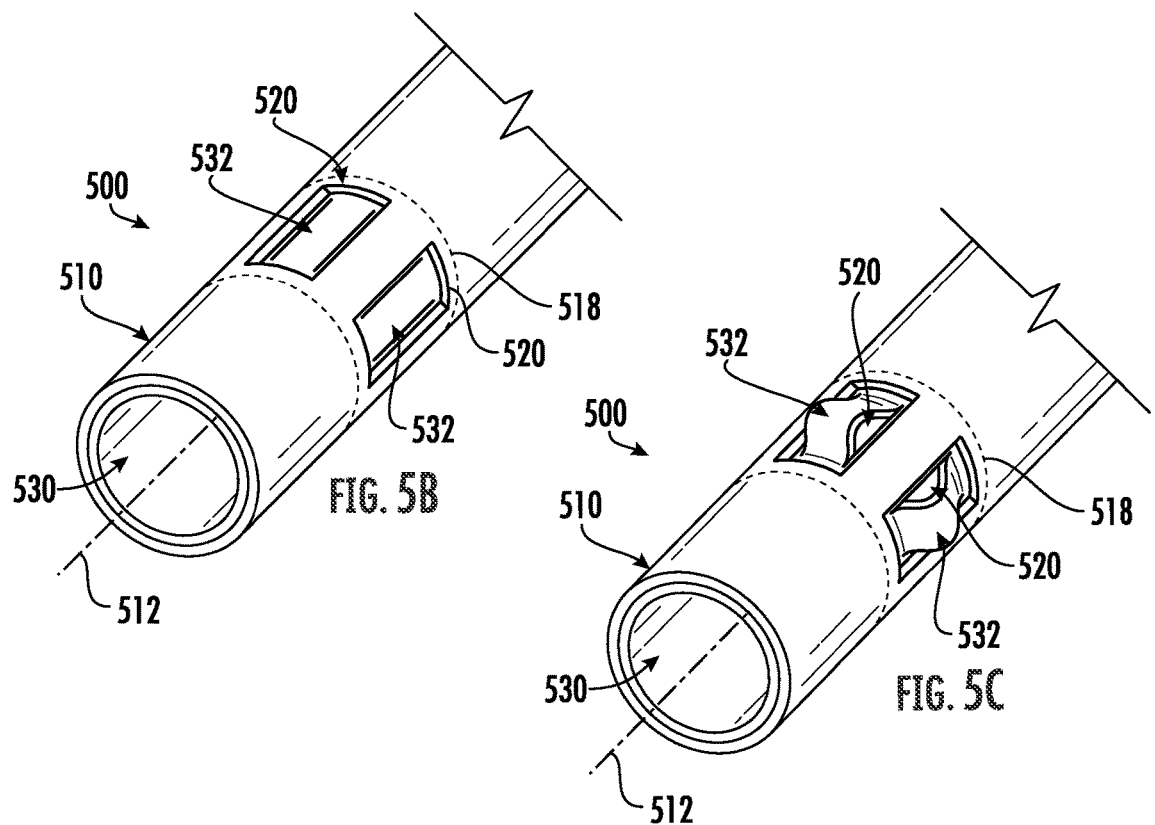
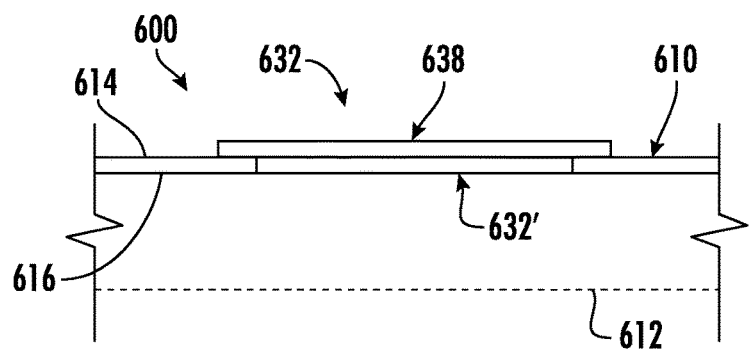
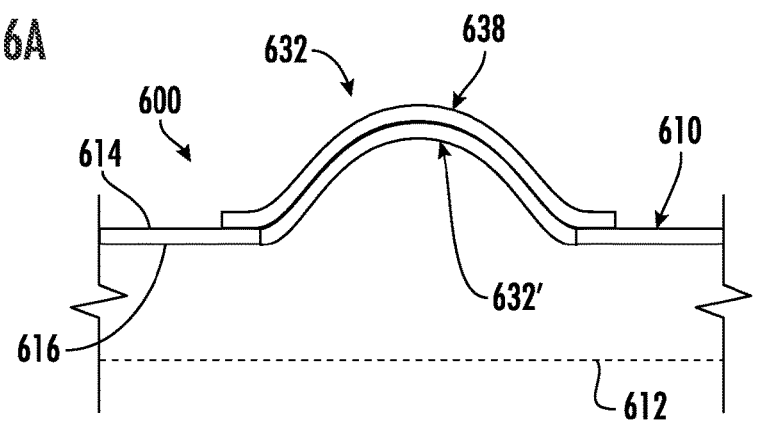

ANCHORING DEVICE

CROSS-REFERENCE TO RELATED APPLICATIONS

This application claims the benefit of U.S. Provisional Patent Application No. 62/947,970, filed Dec. 13, 2019, the contents of which are incorporated herein by reference in their entirety.

BACKGROUND

Current coupling devices for medical implants, such as for femoral stems used in total hip arthroplasty, are inserted into the medullary cavity of a femur and are coupled to the femur either by fasteners, pins, adhesive, or friction fit. However, certain coupling techniques can cause adverse reactions, which can lead to complications and/or longer recovery times for the patient. Some coupling techniques can also allow the implant to become loose within the medullary cavity over time.

Furthermore, current coupling devices can be difficult to replace during re-surgery, which can cause damage to the bone of the patient during removal and reimplantation.

Thus, a need exists for an implant coupling device that is less susceptible to adverse reactions, will stay rigidly coupled to a bone over time, and can be removed and reimplanted during re-surgery without damaging the bone of the patient.

SUMMARY

Various implementations include an anchoring device. The device includes a tubular body and at least one anchor. The tubular body has a longitudinal axis, an outer surface, and an inner surface opposite and radially spaced apart from the outer surface. An axially extending section of the body defines at least one opening extending from the outer surface to the inner surface. The at least one opening has a first axial end and a second axial end opposite and spaced apart from each other along the longitudinal axis. The at least one anchor extends along the opening between the first axial end and the second axial end of the opening. The at least one anchor includes a shape memory material. The at least one anchor is movable from a retracted position to an extended position by either increasing the temperature of the anchor above an austenite finishing temperature or decreasing the temperature of the anchor below a martensite finishing temperature. The anchor has a smaller radius of curvature in a plane that includes the longitudinal axis in the extended position than in the retracted position.

In some implementations, the at least one anchor further includes a resilient member that is biased toward the extended position and urgable toward the retracted position. The shape memory material of the at least one anchor urges the resilient member toward the retracted position when the anchor is above the austenite finishing temperature and allows the resilient member to move toward the extended position when the anchor is below the martensite finishing temperature.

In some implementations, the body includes a shape memory material. In some implementations, the body and the anchor are integrally formed. In some implementations, the body includes a single piece of formed shape memory material foil.

In some implementations, the device further includes a tubular inner sleeve defining the at least one anchor. The inner sleeve is configured to be disposed relative to the body such that the at least one anchor is extendable through the at least one opening in the extended position. In some implementations, the inner sleeve includes a single piece of formed shape memory material foil.

In some implementations, the body includes a material with a higher modulus of elasticity than the at least one anchor. In some implementations, the body includes a porous material. In some implementations, the body includes a biocompatible material.

In some implementations, the at least one anchor extends parallel to the longitudinal axis. In some implementations, the at least one anchor extends circumferentially as it extends in an axial direction such that the anchors extend helically around the body of the device.

In some implementations, a cross-section of the body as viewed in a plane perpendicular to the longitudinal axis is circular.

In some implementations, the body includes two axially extending sections, and each of the two axially extending sections defines two or more circumferentially spaced openings.

In some implementations, the anchor is curved radially outwardly along the axial direction in the extended position. In some implementations, the anchor is not curved along the axial direction in the retracted position.

In some implementations, the axially extending section of the body defines at least three circumferentially spaced openings and the device includes at least three anchors.

In some implementations, the shape memory material is NiTi.

In some implementations, one of the inner surface and the outer surface includes a coating comprising polyethylene terephthalate ("PET").

Various other implementations include a method for creating an anchoring device. The method includes (1) forming a material into a tubular body, the body having a longitudinal axis, an outer surface, and an inner surface opposite and radially spaced apart from the outer surface; (2) defining at least one opening in an axially extending section of the body, wherein each of the at least one opening extends from the outer surface to the inner surface, the at least one opening having a first axial end and a second axial end opposite and spaced apart from each other along the longitudinal axis; (3) forming at least one anchor extending along the opening between the first axial end and the second axial end of the opening, wherein the at least one anchor comprises a shape memory material; and (4) increasing the temperature of the at least one anchor above a shape setting temperature of the shape memory material to set either an extended position or a retracted position of the at least one anchor. The at least one anchor is movable from the extended position to the retracted position by either increasing the temperature of the anchor above an austenite finishing temperature or decreasing the temperature of the anchor below the martensite finishing temperature. The anchor has a smaller radius of curvature in a plane that includes the longitudinal axis in the extended position than in the retracted position.

In some implementations, the method further includes deforming the at least one anchor into the extended position prior to increasing the temperature of the at least one anchor above the shape setting temperature, and the method further includes decreasing the temperature of the at least one anchor below a martensite finishing temperature of the shape memory material and deforming the at least one anchor from the extended position to the retracted position.

In some implementations, increasing the temperature of the at least one anchor above a shape setting temperature of the shape memory material sets the retracted position of the at least one anchor, and the at least one anchor further includes a resilient member that is biased toward the extended position and urgable toward the retracted position. The shape memory material of the at least one anchor urges the resilient member toward the retracted position when the anchor is above the austenite finishing temperature and allows the resilient member to move toward the extended position when the anchor is below the martensite finishing temperature.

In some implementations, the body comprises a shape memory material. In some implementations, the body and the anchor are integrally formed. In some implementations, the body includes a single piece of formed shape memory material foil.

In some implementations, wherein a tubular inner sleeve defines the at least one anchor, and the method further includes, after deforming the at least one anchor from the extended position to the retracted position, disposing the inner sleeve relative to the body such that the at least one anchor is extendable through the at least one opening in the extended position. In some implementations, the inner sleeve includes a single piece of formed shape memory material foil.

In some implementations, the body includes a material with a higher modulus of elasticity than the at least one anchor. In some implementations, the body includes a porous material. In some implementations, the body includes a biocompatible material.

In some implementations, the at least one anchor extends parallel to the longitudinal axis. In some implementations, the at least one anchor extends circumferentially as it extends in an axial direction such that the anchors extend helically around the body of the device.

In some implementations, a cross-section of the body as viewed in a plane perpendicular to the longitudinal axis is circular.

In some implementations, the body includes two axially extending sections, and two or more circumferentially spaced openings are defined in each of the two axially extending sections.

In some implementations, the anchor is curved radially outwardly along the axial direction in the extended position. In some implementations, the anchor is not curved along the axial direction in the retracted position.

In some implementations, the axially extending section of the body defines at least three circumferentially spaced openings and the device includes at least three anchors.

In some implementations, the shape memory material is NiTi.

In some implementations, one of the inner surface and the outer surface includes a coating comprising polyethylene terephthalate ("PET").

Various other implementations include a method of coupling an anchoring device to an object. The method includes (1) obtaining an anchoring device, such as the anchoring device described above; (2) disposing an object having a longitudinal axis relative to the anchoring device such that at least a portion of one of the object and the anchoring device is disposed within the other of the anchoring device and the object; and (3) either increasing the temperature of the anchor above the austenite finishing temperature or decreasing the temperature of the anchor below the martensite finishing temperature to move the anchor from the retracted position to the extended position. The anchor abuts the object in the extended position.

In some implementations, the at least one anchor further includes a resilient member that is biased toward the extended position and urgable toward the retracted position. The shape memory material of the at least one anchor urges the resilient member toward the retracted position when the anchor is above the austenite finishing temperature and allows the resilient member to move toward the extended position when the anchor is below the martensite finishing temperature.

In some implementations, the body includes a shape memory material. In some implementations, the body and the anchor are integrally formed. In some implementations, the body includes a single piece of formed shape memory material foil.

In some implementations, a tubular inner sleeve defines the at least one anchor, and the inner sleeve is configured to be disposed relative to the body such that the at least one anchor is extendable through the at least one opening in the extended position. In some implementations, the inner sleeve includes a single piece of formed shape memory material foil.

In some implementations, the body includes a material with a higher modulus of elasticity than the at least one anchor. In some implementations, the body includes a porous material. In some implementations, the body includes a biocompatible material.

In some implementations, the at least one anchor extends parallel to the longitudinal axis. In some implementations, the at least one anchor extends circumferentially as it extends in an axial direction such that the anchors extend helically around the body of the device.

In some implementations, a cross-section of the body as viewed in a plane perpendicular to the longitudinal axis is circular.

In some implementations, the body includes two axially extending sections, and two or more circumferentially spaced openings are defined in each of the two axially extending sections.

In some implementations, the anchor is curved radially outwardly along the axial direction in the extended position. In some implementations, the anchor is not curved along the axial direction in the retracted position.

In some implementations, the axially extending section of the body defines at least three circumferentially spaced openings and the device includes at least three anchors.

In some implementations, the shape memory material is NiTi.

In some implementations, one of the inner surface and the outer surface includes a coating comprising polyethylene terephthalate ("PET").

In some implementations, the object includes a bone. In some implementations, the anchoring device is disposed within a medullary cavity of the bone.

In some implementations, the object includes a pipe. In some implementations, the pipe is disposed within the anchoring device.

BRIEF DESCRIPTION OF DRAWINGS

Example features and implementations are disclosed in the accompanying drawings. However, the present disclosure is not limited to the precise arrangements and instrumentalities shown.

FIG. 5B is a perspective view of a retracted position of the anchoring device of FIG. 5A.

FIG. 5C is a perspective view of an extended position of the anchoring device of FIG. 5A.

FIG. 6A is a perspective view of a retracted position of an anchoring device, according to another implementation.

FIG. 6B is a perspective view of an extended position of the anchoring device of FIG. 6A.

DETAILED DESCRIPTION

Figure 1:
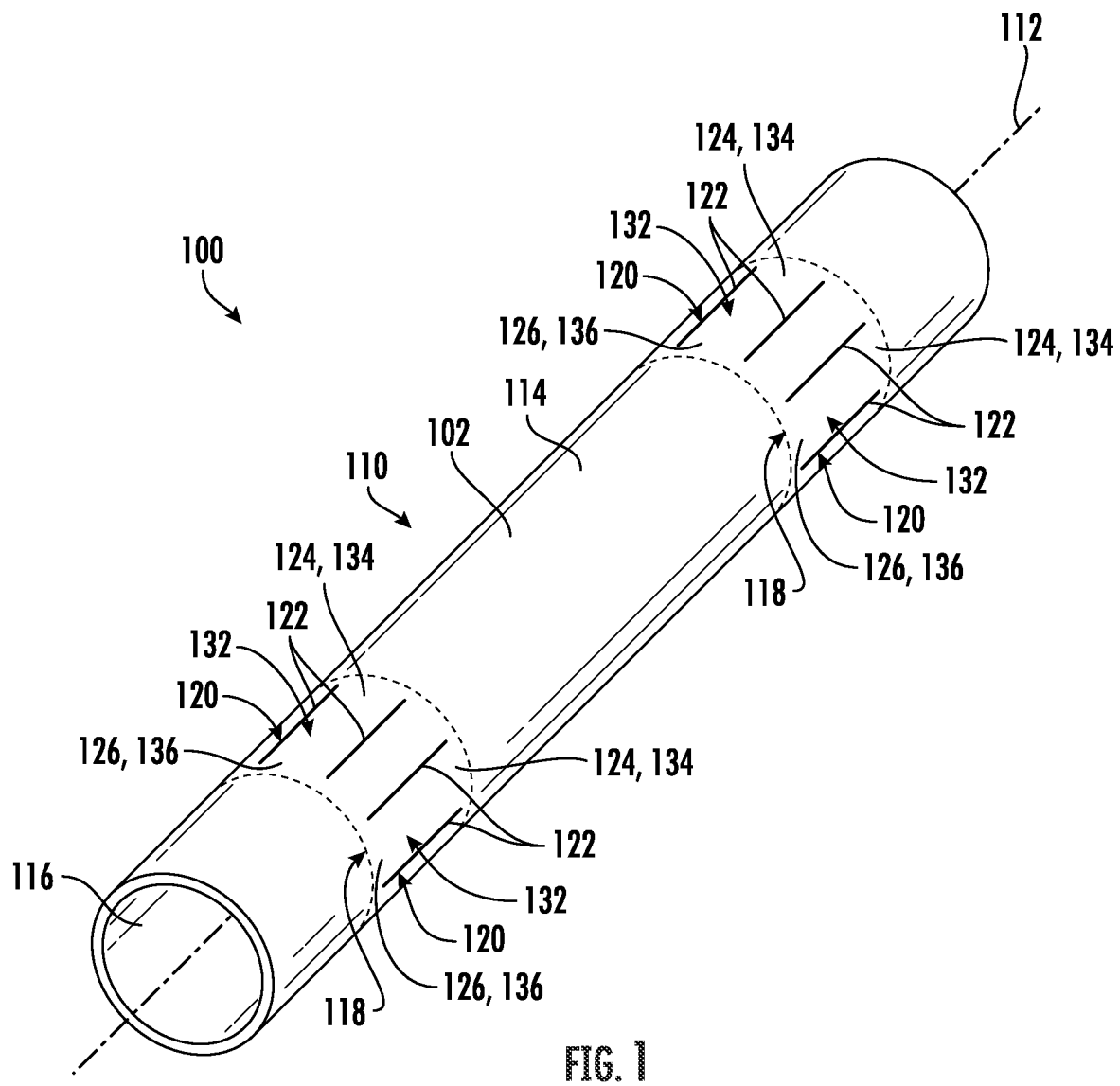
FIG. 1 is a perspective view of an anchoring device, according to one implementation.

The devices, systems, and methods disclosed herein provide for an anchoring device with extendable anchors. The anchors include a shape memory material that is configured to move the anchors to an extended position when the temperature of the device is either increased above the austenite finishing temperature or decreased below the martensite finishing temperature of the shape memory material. An object, such as a bone or a pipe, can be disposed relative to the anchoring device such that when the anchors are extended, the anchors rigidly abut the surfaces of the object to couple the anchoring device to the object. The device can also be used for quick changing of tires, as an axle of a vehicle, paper roll dispensers, or any other situation where coupling and uncoupling of objects is desired. The device can also include multiple coupling portions for coupling multiple objects together.

When the anchoring device is incorporated into a medical implant and the anchoring device is inserted into the medullary cavity of a bone, the device can be heated to cause the anchors to extend and unobtrusively and rigidly couple the implant to the bone. In some implementations, the anchors move to the extended position when the temperature of the device is increased above the austenite finishing temperature, and the austenite finishing temperature is below the patient's body temperature. The device can be kept below the austenite finishing temperature until the implant is disposed within the medullary cavity of the bone, and the patient's internal body temperature causes the anchors to move to the extended position.

When the devices, systems, and methods disclosed herein are used as a coupler for medical implants, the device can be easily removed and reimplanted during re-surgery without damaging the bone of a patient. The temperature of the shape memory material anchors can be either be increased or decreased to release the rigid, extended position of the anchors to allow the implant to be uncoupled from the bone.

Various implementations include an anchoring device. The device includes a tubular body and at least one anchor. The tubular body has a longitudinal axis, an outer surface, and an inner surface opposite and radially spaced apart from the outer surface. An axially extending section of the body defines at least one opening extending from the outer surface to the inner surface. The at least one opening has a first axial end and a second axial end opposite and spaced apart from each other along the longitudinal axis. The at least one anchor extends along the opening between the first axial end and the second axial end of the opening. The at least one anchor includes a shape memory material. The at least one anchor is movable from a retracted position to an extended position by either increasing the temperature of the anchor above an austenite finishing temperature or decreasing the temperature of the anchor below a martensite finishing temperature. The anchor has a smaller radius of curvature in a plane that includes the longitudinal axis in the extended position than in the retracted position.

Various other implementations include a method for creating an anchoring device. The method includes (1) forming a material into a tubular body, the body having a longitudinal axis, an outer surface, and an inner surface opposite and radially spaced apart from the outer surface; (2) defining at least one opening in an axially extending section of the body, wherein each of the at least one opening extends from the outer surface to the inner surface, the at least one opening having a first axial end and a second axial end opposite and spaced apart from each other along the longitudinal axis; (3) forming at least one anchor extending along the opening between the first axial end and the second axial end of the opening, wherein the at least one anchor comprises a shape memory material; and (4) increasing the temperature of the at least one anchor above a shape setting temperature of the shape memory material to set either an extended position or a retracted position of the at least one anchor. The at least one anchor is movable from the extended position to the retracted position by either increasing the temperature of the anchor above an austenite finishing temperature or decreasing the temperature of the anchor below the martensite finishing temperature. The anchor has a smaller radius of curvature in a plane that includes the longitudinal axis in the extended position than in the retracted position.

Various other implementations include a method of coupling an anchoring device to an object. The method includes (1) obtaining an anchoring device, such as the anchoring device described above; (2) disposing an object having a longitudinal axis relative to the anchoring device such that at least a portion of one of the object and the anchoring device is disposed within the other of the anchoring device and the object; and (3) either increasing the temperature of the anchor above the austenite finishing temperature or decreasing the temperature of the anchor below the martensite finishing temperature to move the anchor from the retracted position to the extended position. The anchor abuts the object in the extended position.

FIGS. 1-3B show an example of an anchoring device 100 according to one implementation. As seen in FIG. 1, the anchoring device 100 includes a tubular body 110 and multiple anchors 132. The tubular body 110 has a longitudinal axis 112, an outer surface 114, and an inner surface 116 opposite and radially spaced apart from the outer surface 114. The cross-section of the body 110 as viewed in a plane perpendicular to the longitudinal axis 112 is circular, but in other implementations, the cross section of the body can be a triangle, a rectangle, a pentagon, a hexagon, an octagon, or any other desired shape. The body 110 includes two axially extending sections 118 that define a series of openings 120. Each of the openings 120 is defined by parallel slits 122 that extend parallel to the longitudinal axis 112 and extend from the outer surface 114 to the inner surface 116 of the body 110. Each of the openings 120 has a first axial end 124 and a second axial end 126 opposite and spaced apart from the first axial end 124 along the longitudinal axis 112.

An anchor 132 extends along each of the openings 120. Each anchor 132 includes a first anchor end 134 and a second anchor end 136 opposite and spaced apart from the first anchor end 134. The first anchor end 134 is coupled to the first axial end 124 of the opening 120, and the second anchor end 136 is coupled to the second axial end 126 of the opening 120.

Because the parallel slits 122 defining each of the openings 120 extend parallel to the longitudinal axis 112, each of the anchors 132 extending from the first axial ends 124 to the second axial ends 126 of the openings 120 also extend parallel to the longitudinal axis 112. However, in other implementations, the parallel slits defining each of the openings extend in a direction that has a circumferential component and an axial component. Thus, in these implementations, each of the anchors extending from the first axial ends to the second axial ends of the openings also extends in the direction that has a circumferential component and an axial component such that the anchors extend helically around the body of the device. In other implementations, the anchors can be designed to extend in any direction to allow for better coupling to specific surfaces.

Although the device 100 shown in FIGS. 1-3B includes two axially extending sections 118 that define openings 120, in other implementations, the device can include only one, or more than two, axially extending sections. The device 100 shown in FIGS. 1-3B includes three openings 120 and anchors 132 in each of the two axially extending sections 118, but in other implementations, the device can include any number of openings and anchors in each of the axially extending sections.

The body 110 and the anchors 132 are both made of Nitinol ("NiTi"). NiTi is a shape memory material, which allows the anchors 132 to be articulated from a retracted position to an extended position by increasing the temperature of the anchor 132 above an austenite finishing temperature. In the extended position, the anchor 132 has a smaller radius of curvature in a plane that includes the longitudinal axis 112 than in the retracted position.

The body 110 and the anchors 132 of the device 100 shown in FIGS. 1-3B are integrally formed. However, in some implementations, the body and the anchors are separately formed and are coupled to each other.

Figure 2:
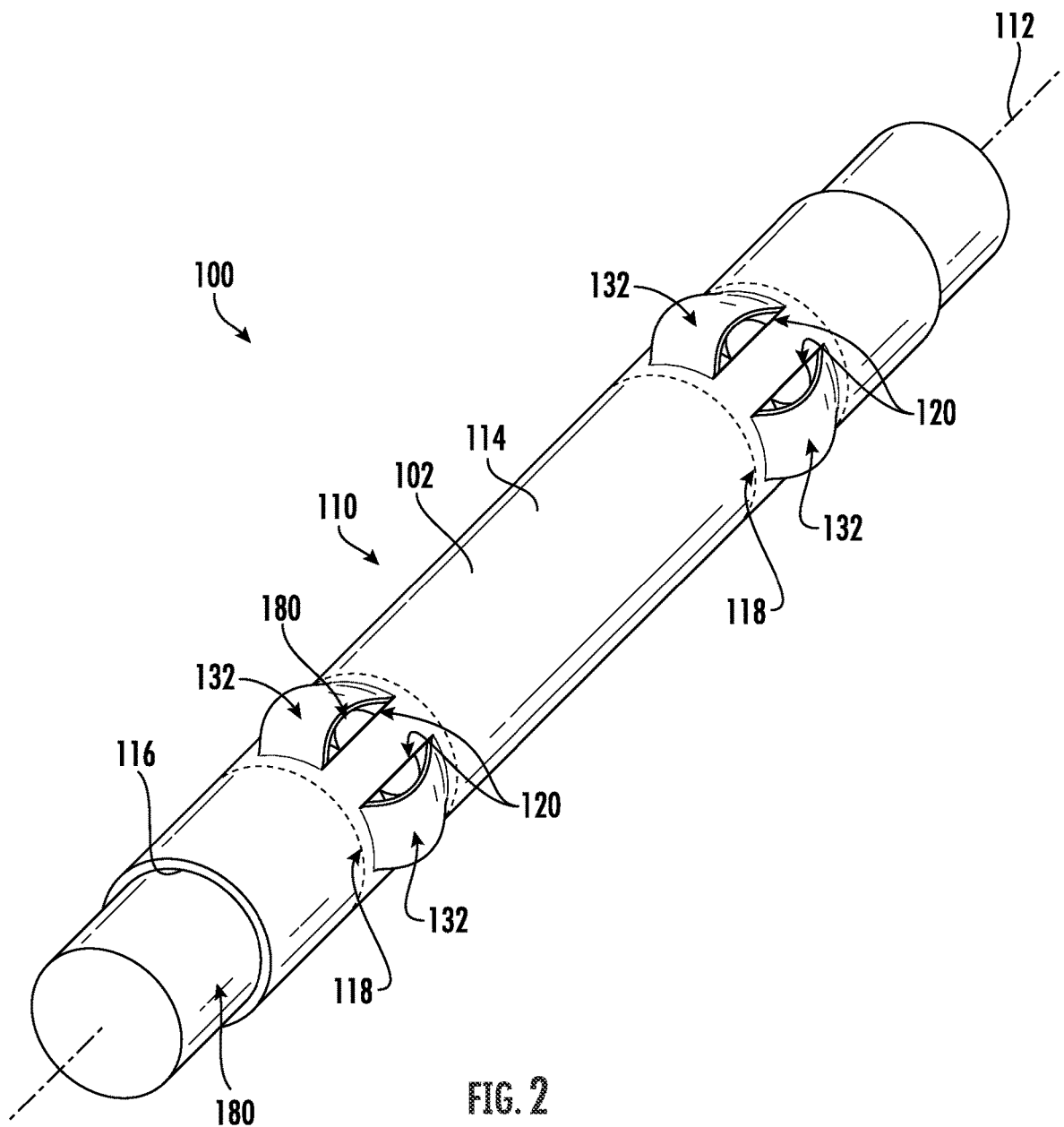
FIG. 2 is a perspective view of a first step in the manufacturing of the anchoring device of FIG. 1, according to one implementation.

FIG. 2 show the steps for manufacturing the device 100 shown in FIG. 1. A sheet of NiTi is first cooled such that the temperature of the sheet of NiTi is below the martensite finishing temperature. In some implementations, the martensite finishing temperature may be higher than room temperature such that the NiTi sheet is already below the martensite finishing temperature and no cooling is necessary. While the NiTi sheet is at or below the martensite finishing temperature of the shape memory material, the NiTi material is malleable and can be formed into a shape.

The sheet of NiTi is then formed into a tubular body 110 by wrapping the NiTi sheet around a cylindrical form 180. Slits 122 are cut through the NiTi sheet of the body 110 to define at least one opening 120 in an axially extending section 118 of the body 110, as shown in FIG. 2. Each of the openings 120 is defined by parallel slits 122 that extend parallel to the longitudinal axis 112 and extend from the outer surface 114 to the inner surface 116 of the body 110. The remaining portion of the NiTi sheet between each pair of adjacent slits 122 of the opening 120 define an anchor 132 that extends along the opening 120 between the first axial end 124 and the second axial end 126 of the opening 120. While the device 100 is still at, or below, a martensite finishing temperature of the shape memory material, each anchor 132 is deformed into an extended position in which the anchors 132 are curved radially outwardly along the axial direction, as shown in FIG. 2.

The device 100 is then heated (e.g., in an oven or kiln) such that the temperatures of the anchors 132 are above the shape setting temperature of the NiTi material. Once the shape setting temperature of the shape memory material has been reached, the austenite, extended position of the anchors 132 of the device 100 are set. The device 100 is then allowed to cool (either actively or passively at room temperature) such that the temperature of the anchors 132 decrease below the martensite finishing temperature of the NiTi material. Once the temperature of the anchors 132 of the device 100 decrease below the martensite finishing temperature, the NiTi material becomes malleable enough to allow the anchors 132 to be deformed back from the extended position to the retracted position, as shown in FIG. 1, in which the anchors 132 are not curved along the axial direction.

Figure 3A:
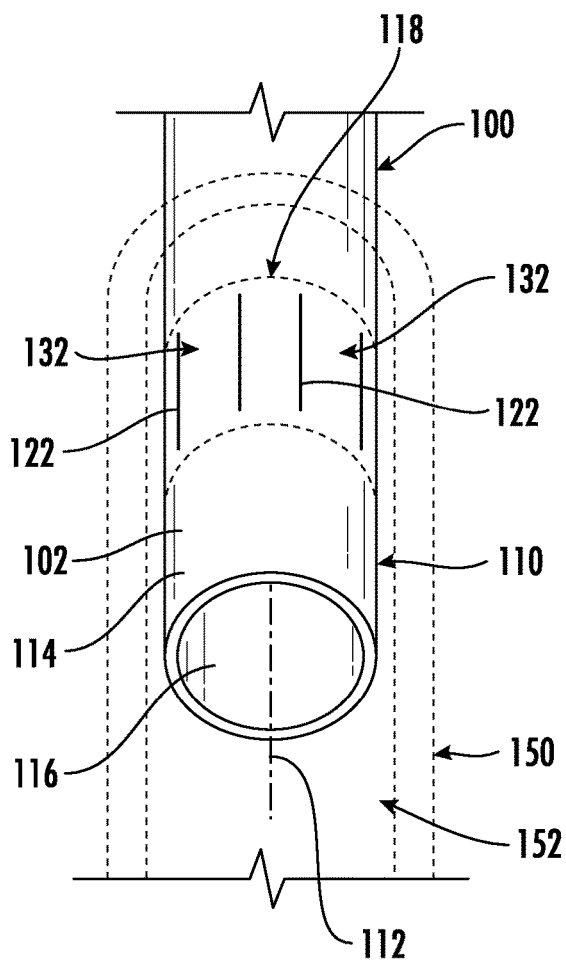
FIG. 3A is a perspective view of a first step of coupling the anchoring device of FIG. 1 to an object, according to one implementation.
Figure 3B:
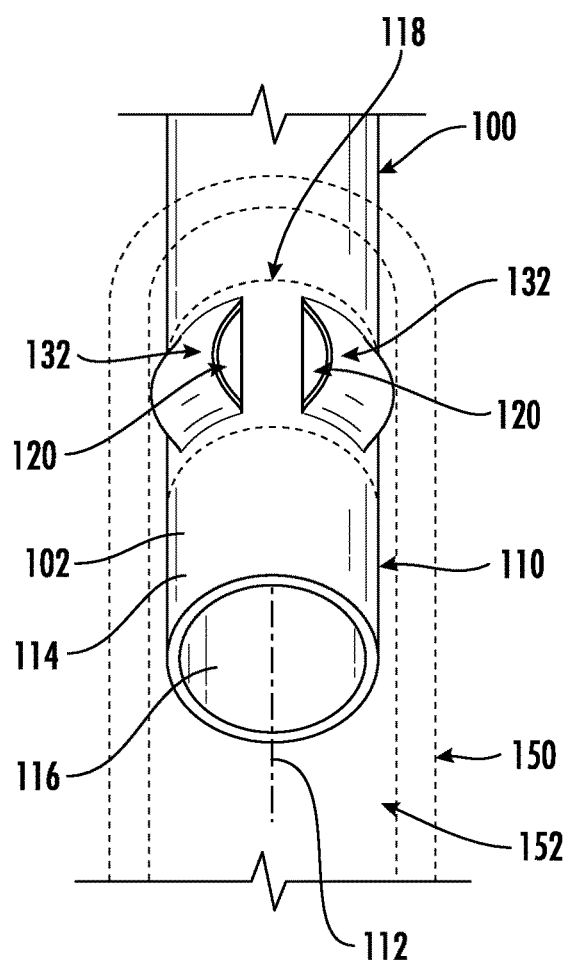
FIG. 3B is a perspective view of a second step of coupling the anchoring device of FIG. 1 to an object, according to the implementation of FIG. 3A.

FIGS. 3A and 3B show the device 100 of FIGS. 1-3B being coupled to an object 150, such as a femur. However, in other implementations, the device shown in FIGS. 1-3B can be coupled to any partially or fully hollow object. To couple the anchoring device 100 to one or more objects 150 (e.g., a medullary cavity of a bone or the inside of a pipe), the temperatures of the anchors 132 of the device 100 are adjusted to below, or ensured that the temperatures are below, the martensite finishing temperature such that the anchors 132 of the device 100 are in the retracted position. Then, at least a portion of the anchoring device 100 is disposed inside the opening 152 of one object 150, as shown in FIG. 3A. If the device 100 is to be coupled to two objects 150, each end of the anchoring device 100 is disposed within an opening 152 in each object 150. In both instances, the axially extending sections 118 on either end of the body 110 are disposed within the opening(s) 152 of the object(s) 150 such that the anchors 132 can contact the walls of the opening(s) 152.

Next, the temperatures of the anchors 132 of the device 100 are increased above the austenite finishing temperature. When the temperature of the device 100 reaches the austenite finishing temperature, the shape memory property of the NiTi anchors reverts the anchors 132 back from the retracted position to their previously shape-set, extended position (i.e., the austenite position), as shown in FIG. 3B. The anchors 132 in their extended positions abut the inner walls of the opening 152 of the object 150. In the austenite state, the NiTi material of the anchors 132 becomes much more rigid relative to the NiTi material when in the martensite state of the retracted position. Thus, when the anchors 132 extend radially outwardly to abut the wall of the opening 152 in the object 150 while in the extended position, the rigidity of the anchors 132 locks the anchoring device 100 into place with a friction fit. When each end of the device 100 is disposed in separate objects 150, the anchoring device 100 can be used to couple the separate objects 150 together.

Figures 4, 5A:
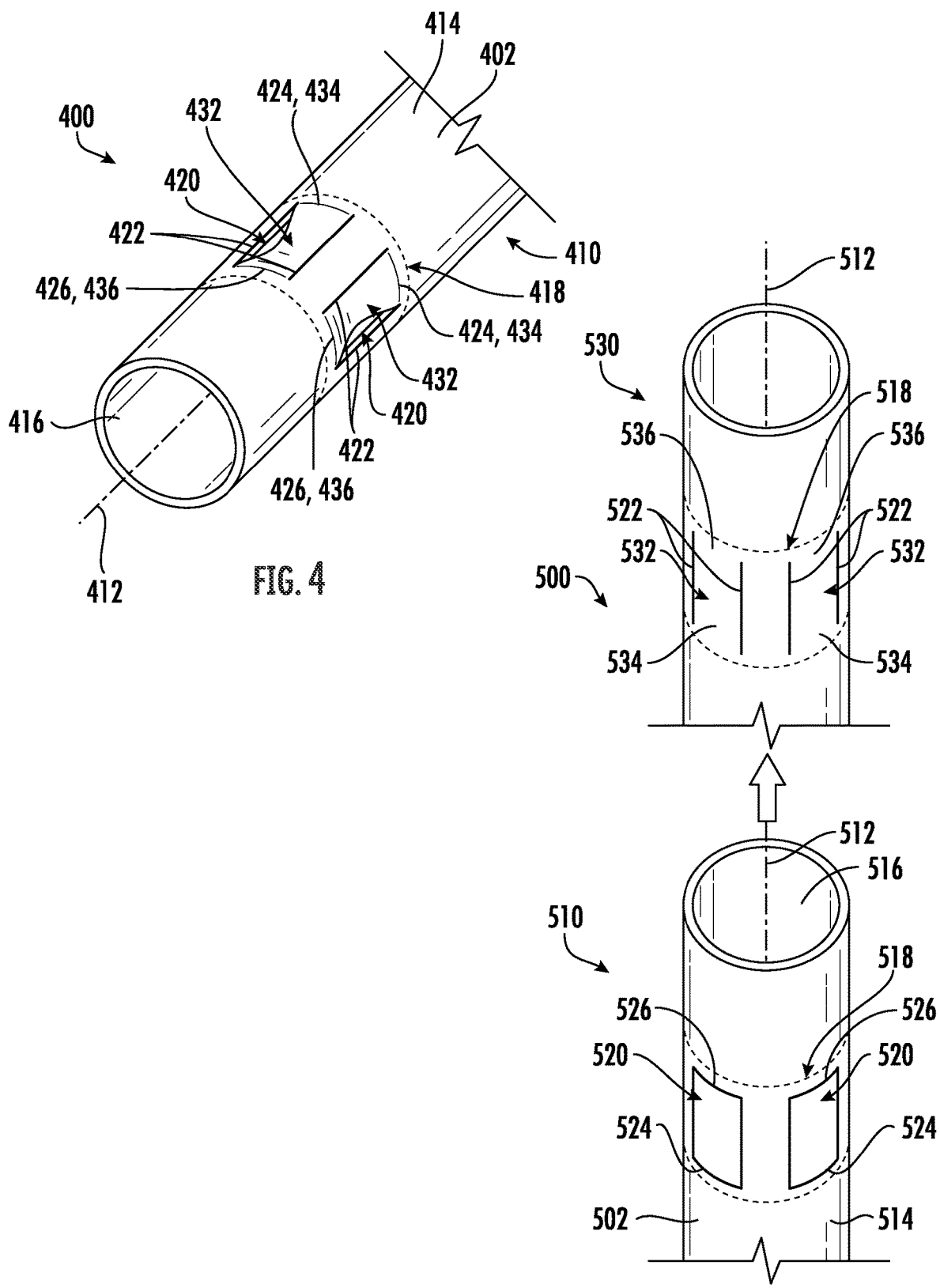
FIG. 4 is a perspective view of an anchoring device, according to another implementation.
FIG. 5A is an exploded perspective view of an anchoring device, according to another implementation.

FIG. 4 shows another implementation of an anchoring device 400. The device 400 shown in FIG. 4 is similar to the anchoring device 100 shown in FIGS. 1-3B, but the anchoring device 400 shown in FIG. 4 includes anchors 432 that extend radially inwardly in the extended position. Similar reference numbers are used for the anchoring device 400 shown in FIG. 4 for features that are similar to those of the anchoring device 100 shown in FIGS. 1-3B. The extended position and retracted position are set in a similar way as described above for the anchoring device 100 shown in FIGS. 1-3B, but with the anchors 432 being deformed radially inwardly in the extended position shown in FIG. 4.

The device 400 shown in FIG. 4 can be coupled to one or more objects 450 by disposing at least a portion of the one or more objects 450 inside the tubular body 410 of the device 400 while the device 400 is below the martensite finishing temperature. If the device 400 is to be coupled to two objects 450, a portion of each of the objects 450 is disposed within an end of the anchoring device 400. Then, the temperatures of the anchors 432 of the device 400 are increased above the austenite finishing temperature such that the NiTi anchors 432 move from the retracted position to their previously shape-set, extended position shown in FIG. 4. The anchors 432 in their radially inwardly extended positions abut the outer walls of the object(s) 450 to rigidly lock the anchoring device 400 into place with a friction fit.

FIGS. 5A-5C show another implementation of an anchoring device 500. Unlike the anchoring device 100 shown in FIGS. 1-3B, the anchoring device 500 shown in FIGS. 5A-5C includes a body 510 that is separately formed from the anchors 532. Similar reference numbers are used for the anchoring device 500 shown in FIGS. 5A-5C for features that are similar to those of the anchoring device 100 shown in FIGS. 1-3B. The device 500 includes a tubular body 510 and a tubular inner sleeve 530.

The inner sleeve 530 of the device 500 shown in FIGS. 5A-5C is made of a single piece of formed shape memory material such as NiTi. The inner sleeve 530 shown in FIG. 5A defines anchors 532 in the same way that the body 110 of the device 100 shown in FIGS. 1-3B defines the openings 120 and anchors 132. However, in other implementations, the anchors and inner sleeve are formed separately and the anchors are coupled to the inner sleeve. In such implementations, the inner sleeve can be made of any material and the anchors are made of a shape memory material.

The body 510 has a longitudinal axis 512, an outer surface 514, and an inner surface 516 opposite and radially spaced apart from the outer surface 514. The body 510 includes two axially extending sections 518 that define a series of openings 520. Each of the openings 520 extend from the outer surface 514 to the inner surface 516 of the body 510 and has a first axial end 524 and a second axial end 526 opposite and spaced apart from the first axial end 524.

When assembled, the inner sleeve 530 is disposed within the hollow tubular body 510, as shown in FIG. 5A. As seen in FIG. 5B, the openings 520 defined by the body 510 are located such that, when the inner sleeve 530 is disposed within the tubular body 510, each of the anchors 532 are aligned with an opening 520 such that each anchor 532 extends along each of the openings 520 from the first axial end 524 to the second axial end 526. When the anchors 532 are moved from the retracted position shown in FIG. 5B to the extended position shown in FIG. 5C, the anchors 532 extend radially outwardly through their respective opening 520.

The extended position and retracted position of the anchors 532 are set in a similar way as described above for the anchoring device 100 shown in FIGS. 1-3B by heating and cooling the inner sleeve 530 rather than the entire device 500. The inner sleeve 530 can be disposed within the body 510 before or after the shape setting process. The device 500 can also be coupled to one or more objects 550 in a similar way as described above for the anchoring device 100 shown in FIGS. 1-3B.

Although the sleeve 530 of the device 500 shown in FIGS. 5A-5C is an inner sleeve 530, in other implementations, the sleeve is a tubular outer sleeve and the body defining one or more openings can be disposed within the outer sleeve. The anchors of the outer sleeve in these implementations would be shape set similarly to the anchors of the device shown in FIG. 4 such that the anchors extend radially inwardly when in the extended position.

FIGS. 6A and 6B show another implementation of anchors 632 of an anchoring device 600. Unlike the anchors 132 shown in FIGS. 1-3B, the anchors 632 of the anchoring device 600 shown in FIGS. 6A and 6B include resilient members 638. Similar reference numbers are used for the anchoring device 600 shown in FIGS. 6A and 6B for features that are similar to those of the anchoring device 100 shown in FIGS. 1-3B.

Each of the anchors 632 of the device 600 shown in FIGS. 6A and 6B include a resilient member 638 and shape memory material portion 632' comprising NiTi. The resilient member 638 is a strip of resilient material that is coupled to the body 610 and shape memory material portion 632' of the anchor 632. The resilient member 638 is biased toward the extended position and urgable toward the retracted position.

A sheet of NiTi at or below the martensite finishing temperature is formed into a tubular body 610 by wrapping the NiTi sheet around a cylindrical form 680, and slits 622 are cut through the NiTi sheet to define at least one opening 620 and a shape memory material portion 632' of an anchor 632, similar to the device 100 shown in FIGS. 1-3B. However, unlike the device 100 shown in FIGS. 1-3B, each anchor 632 is then deformed into a retracted position in which the anchors 632 are not curved along the axial direction, and the device 600 is heated to the shape setting temperature to set the austenite, extended position of the shape memory material portion 632' of the anchors 632 of the device 600.

Because the resilient member 638 is urgable toward the retracted position of the anchor 632, and the shape memory material portion 632' of the anchor 632 is rigid and not curved along the axial direction in the austenite state, the resilient member 638 is urged toward the retracted position when the temperature of the device 600 is above the austenite finishing temperature, as shown in FIG. 6A. Once the temperature of the device 600 is cooled below the martensite finishing temperature, the shape memory material portion 632' of the anchors 632 become malleable and allow the resilient members 638 to move toward their biased extended position, as shown in FIG. 6B. Thus, while the anchoring device 100 shown in FIGS. 1-3B moves from the retracted position to the extended position when the temperature of the anchors 132 increases above the austenite finishing temperature, the implementation of an anchoring device 600 shown in FIGS. 6A and 6B moves from the retracted position to the extended position when the temperature of the anchors 632 decreases below the martensite finishing temperature.

In some implementations, the anchors 632 shown in FIGS. 6A and 6B can be used in place of or in combination with the anchors of any of the implementations disclosed herein. Although the resilient member 638 shown in FIGS. 6A and 6B is a strip of resilient material coupled to the body 610 and shape memory material portion 632' of the anchor 632, in other implementations, the resilient member is a spring or any other device that is capable of biasedly moving the anchor toward the extended position when the shape memory material portion is in the martensite state.

The bodies 110, 410, 510, 610 shown in each of the above described anchoring devices 100, 400, 500, 600 includes a polyethylene terephthalate ("PET") coating 102, 402, 502, 602. PET is biocompatible and has a higher modulus of elasticity than NiTi. The PET coating is also designed to be porous to promote bone growth and bonding. Although the coating 102, 402, 502, 602 shown in these figures is PET, any material coating having any of these desirable features can be used. In some implementations, the outer surface of the body, the anchors, and/or the outer sleeve include a PET coating. In implementations in which the inner surface of the device is meant to abut an object during coupling, the coating can be applied to the inner surfaces of the body, anchors, and/or inner sleeve. In implementations in which the body and anchors are separately formed, the body may be made of, or partially made of, PET, and the anchors are made of a shape memory material.

Although portions of the devices 100, 400, 500, 600 disclosed herein comprise NiTi, in other implementations, one or more portions of the device comprise any shape memory material. In some implementations, one or more portions of the device comprise any shape memory metal. In some implementations, one or more portions of the device comprise any shape memory metal. In some implementations, one or more portions of the device comprise Ti—Ni—Pd, Ti—Ni—Pt, Ni—Ti—Hf, Ni—Ti—Zr, Cu—Al—Ni, Cu—Al—Nb, Co—Al, Co—Ni—Al, Ni—Al, Ni—Mn, Ni—Mn—Ga, Zr—Cu, Ti—Nb, U—Nb, Ti—Pd, Ti—Au, Ti—Pt—Ir, Ta—Ru, Nb—Ru, Ni—Ti—Hf—Zr, Ni—Ti—Er, and/or any shape memory alloy. In some implementations, one or more portions of the device comprise any NiTi-based, Cu-based, and/or Fe-based alloys. In some implementations, the shape memory metal portions include a medical grade metal.

Although both ends of each anchor of the devices shown in the figures are coupled to the first and second axial ends of an opening, in some implementations, only a coupled end of each anchor is coupled to either the first or second axial end of the opening and a free end of each anchor is not directly coupled to the body. In these implementations, the anchors do not curve in the extended position. Instead, the anchors are bent at their coupled end relative to the body such that the free end of the anchor is further from the longitudinal axis of the body in the extended position than in the retracted position.

A number of example implementations are provided herein. However, it is understood that various modifications can be made without departing from the spirit and scope of the disclosure herein. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. Although the terms "comprising" and "including" have been used herein to describe various implementations, the terms "consisting essentially of" and "consisting of" can be used in place of "comprising" and "including" to provide for more specific implementations and are also disclosed.

Disclosed are materials, systems, devices, methods, compositions, and components that can be used for, can be used in conjunction with, can be used in preparation for, or are products of the disclosed methods, systems, and devices. These and other components are disclosed herein, and it is understood that when combinations, subsets, interactions, groups, etc. of these components are disclosed that while specific reference of each various individual and collective combinations and permutations of these components may not be explicitly disclosed, each is specifically contemplated and described herein. For example, if a device is disclosed and discussed each and every combination and permutation of the device, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed systems or devices. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

What is claimed is:

1. An anchoring device, the device comprising:
a tubular body having a longitudinal axis, an outer surface, and an inner surface opposite and radially spaced apart from the outer surface, wherein an axially extending section of the body defines two or more openings extending from the outer surface to the inner surface, each of the two or more openings having a first axial end and a second axial end opposite and spaced apart from each other along the longitudinal axis, wherein the two or more openings are circumferentially spaced apart from each other; and
two or more anchors each extending along a separate one of the two or more openings in a circumferential direction and coupled to the first axial end and the second axial end of the respective opening, wherein the two or more anchors comprise a shape memory material,
wherein each of the two or more anchors is movable from a retracted position to an extended position by either increasing the temperature of the anchor above an austenite finishing temperature or decreasing the temperature of the anchor below a martensite finishing temperature, wherein each of the two or more anchors has a smaller radius of curvature in a plane that includes the longitudinal axis in the extended position than in the retracted position,
wherein a portion of the tubular body between the two or more circumferentially spaced openings does not extend when the two or more anchors move from the retracted position to the extended position.

2. The device of claim 1, wherein each of the two or more anchors further includes a resilient member that is biased toward the extended position and urgable toward the retracted position, wherein the shape memory material of each of the two or more anchors urges the resilient member toward the retracted position when the anchor is above the austenite finishing temperature and allows the resilient member to move toward the extended position when the anchor is below the martensite finishing temperature.

3. The device of claim 1, wherein the body comprises a shape memory material.

4. The device of claim 3, wherein the body and the two or more anchors are integrally formed.

5. The device of claim 4, wherein the body comprises a single piece of formed shape memory material foil.

6. The device of claim 1, wherein the body comprises a material with a higher modulus of elasticity than the two or more anchors.

7. The device of claim 1, wherein the body comprises a porous material.

8. The device of claim 1, wherein the body comprises a biocompatible material.

9. The device of claim 1, wherein each of the two or more anchors extends parallel to the longitudinal axis.

10. The device of claim 1, wherein each of the two or more anchors extends in a direction that has a circumferential component and an axial component such that each of the two or more anchors extends helically around the body of the device.

11. The device of claim 1, wherein a cross-section of the body as viewed in a plane perpendicular to the longitudinal axis is circular.

12. The device of claim 1, wherein the body includes two axially extending sections, and each of the two axially extending sections defines two or more circumferentially spaced openings.

13. The device of claim 1, wherein each of the two or more anchors is curved radially outwardly along the axial direction in the extended position.

14. The device of claim 1, wherein each of the two or more anchors is not curved along the axial direction in the retracted position.

15. The device of claim 1, wherein the axially extending section of the body defines at least three circumferentially spaced openings and the device includes at least three anchors.

16. The device of claim 1, wherein the shape memory material is NiTi.

17. The device of claim 1, wherein one of the inner surface and the outer surface includes a coating comprising polyethylene terephthalate ("PET").

* * * * *